United States Patent [19]

McDonald

[11] Patent Number: 5,847,125
[45] Date of Patent: Dec. 8, 1998

[54] AMINO ACID DERIVATIVES WITH ANTICHOLECYSTOKININ ACTIVITY

[75] Inventor: Iain Mair McDonald, Paddock Wood, United Kingdom

[73] Assignee: James Black Foundation Limited, London, England

[21] Appl. No.: 256,145

[22] PCT Filed: Jan. 8, 1993

[86] PCT No.: PCT/GB93/00028

§ 371 Date: Jul. 7, 1994

§ 102(e) Date: Jul. 7, 1994

[87] PCT Pub. No.: WO93/14066

PCT Pub. Date: Jul. 22, 1993

[30] Foreign Application Priority Data

Jan. 9, 1992 [GB] United Kingdom ................ 9200420.9

[51] Int. Cl.⁶ .................... C07D 223/32; C07D 491/113; C07D 317/10

[52] U.S. Cl. ............................ 540/582; 546/16; 546/19; 560/16; 560/24; 560/38; 562/427

[58] Field of Search .............................. 540/582; 546/16, 546/19; 560/16; 562/427

[56] References Cited

U.S. PATENT DOCUMENTS

| | | | |
|---|---|---|---|
| 4,791,102 | 12/1988 | Bernat et al. | 514/19 |
| 4,977,168 | 12/1990 | Bernat et al. | 514/330 |
| 5,064,853 | 11/1991 | Gasc et al. | 514/419 |

FOREIGN PATENT DOCUMENTS

| | | |
|---|---|---|
| 2044636 | 1/1992 | Canada . |
| 0 250 148 | 12/1987 | European Pat. Off. . |
| 0 272 228 | 6/1988 | European Pat. Off. . |
| 0 308 885 | 3/1989 | European Pat. Off. . |
| 0 433 064 | 6/1991 | European Pat. Off. . |
| 87/03869 | 7/1987 | WIPO . |
| 88/05774 | 8/1988 | WIPO . |
| 92/00958 | 1/1992 | WIPO . |

OTHER PUBLICATIONS

Bhatt et al., "Preparation and Antimicrobial Activity Of L[+] β–Aryl. Sulphonamido Succinie Acids and L [+]–Disodium–β–Aryl–Sulphonamido Glutarates", *Indian Chemical Journal*, pp. 21–22, (1978).

*Chemical Abstracts*, vol. 115, No. 19, 98, Nov. 11, 1991 abstract 207671h.

JHA et al., "Possible Antineoplastic Agents: Part XI—QSAR Analogs of Glutamines: Synthesis & Biological Activity Of Some 5–N–Alkyl–2(substituted Benzene-sulphonyl)–L–Glutamines", *Indian Journal Of Chemistry*, vol. 25B:542–545, (1987).

JHA et al., "Possible Antineoplastc Agents X: Synthesis, Antieoplastic Activity and QSAR Study of Some 5–n–Substituted–2–(Chlorosubstituted Benzenesulpho-nyl)–L–Glutamines and 5–N–Alkyl–2–(2', 5'–Dichloroben-zenesulphonyl)–L–Glutamines", *Indian J. Pharm. Sci.*, pp. 133–136, (1986).

DE et al., "Possible Antineoplastic Agents IX: Synthesis, Antineoplastic Activity and Quantitative Structure Activity Relationship Of 5–N–Substituted–2–(Chlorosubstituted Benzenesulphonyl)–L–Glutamines", *Indian J. Pharm. Sci.*, pp. 93–96, (1984).

*Primary Examiner*—Johann Richter
*Assistant Examiner*—Taofiq A. Solola
*Attorney, Agent, or Firm*—Foley & Lardner

[57] ABSTRACT

Compounds of formula (II) wherein Ar is naphthyl, naphthylmethyl, 1,2,3,4-tetrahydronaphthyl, phenethyl, styryl, indanyl or a substituted derivative of any of the foregoing, or 3,4-dichlorophenyl, $R_1$ is H, $C_1$ to $C_6$ alkyl, $C_1$ to $C_6$ alkenyl, cycloalkyl, $-(CH_2)_q$aryl, $-(CH_2)_q$(substituted aryl), $-(CH_2)_q$heterocyclic or $-(CH_2)_q$(substituted heterocyclic), wherein q is 0 to 4, $R_2$ is H, methyl or ethyl, $R_3$ is $C_1$ to $C_3$ alkylene or is absent, T is carboxyl, $-CONR_4R_5$ (wherein $R_4$ and $R_5$ are independently H or $C_1$ to $C_4$ alkyl), $-COOR_{13}$ (wherein $R_{13}$ is $C_1$ to $C_4$ alkyl, benzyl or substituted benzyl) or tetrazolyl, X is $-C(O)-$ or $-CH_2-$, and Y is $-NR_6R_7$ or $-O-R_6$ (wherein $R_6$ and $R_7$ are independently H, $C_1$ to $C_{15}$ hydrocarbyl or halo-substituted $C_1$ to $C_{15}$ hydrocarbyl in which up to 6 carbon atoms may be replaced by $-O-$, $-S-$, or $-NR_8-$ ($R_8$ being absent or selected from H, $C_1$ to $C_{12}$ hydrocarbyl, $C_1$ to $C_{12}$ hydrocarbylcarbonyl and $C_1$ to $C_{12}$ hydrocarbyloxycarbonyl), provided that neither $R_6$ nor $R_7$ contains a $-O-O-$ group, and wherein $R_6$ and $R_7$ may be linked by a single or double bond), and pharmaceutically acceptable salts thereof are ligands at CCK and/or gastrin receptors.

25 Claims, No Drawings

AMINO ACID DERIVATIVES WITH ANTICHOLECYSTOKININ ACTIVITY

This application is a 371 of PCT/GB93/00028 filed Jan. 8, 1995.

This invention relates to amino acid derivatives, and more particularly to amino acid derivatives which possess anticholecystokinin activity. The invention also relates to methods for preparing such cholecystokinin antagonists and to compounds which are useful as intermediates in such methods.

Cholecystokinins are peptides which have been found both in gastrointestinal tissue and in the central nervous system. Natural cholecystokinin is a 33 amino acid peptide (CCK-33), the C-terminal 5 amino acids of which are identical to those of gastrin and caerulein. Also found naturally is the C-terminal octapeptide (CCK-8) of CCK-33.

The cholecystokinins are believed to be important in the regulation of appetite. They stimulate intestinal motility, gall bladder contraction and pancreatic enzyme secretion, and they also inhibit gastric emptying.

A classification scheme for cholecystokinin receptors has recently been proposed in which the receptors coupled to contraction of the gall bladder are termed CCK-A, while those found in the brain are termed CCK-B.

A number of cholecystokinin-receptor antagonists have been reported in the literature. Possible therapeutic uses for CCK-A antagonists include the control of appetite disorders such as anorexia nervosa, and the treatment of pancreatic inflammation, pancreatic cancer, biliary tract disease, Zollinger-Ellison syndrome and various psychiatric disorders. Other possible uses are in the potentiation of opiate (eg. morphine) analgesia, and in the treatment of cancers. Moreover, ligands for CCK-B receptors have been claimed to possess anxiolytic activity.

EP-A-0433064 discloses a class of naphthylsulphonylalkanoic acid compounds which are said to be cholecystokinin antagonists. The compounds are of the general formula

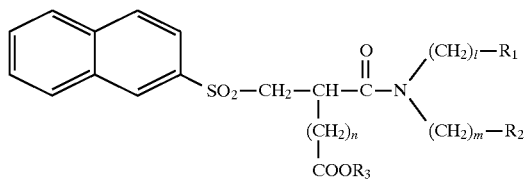

wherein $R_3$ represents a hydrogen atom, an alkyl group having 1 to 4 carbon atoms or a benzyl group; 1 and m are the same or different and are an integer of from 1 to 4; n is 1 or 2; and the definitions of $R_1$ and $R_2$ include groups such as $C_1$ to $C_6$ alkyl, $C_3$ to $C_6$ cycloalkyl and $C_1$ to $C_6$ alkoxy groups.

The present invention is based on the finding that the moiety

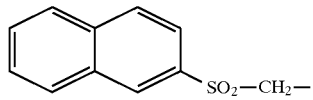

which is an essential element of the compounds disclosed in EP-A-0433064, is not in fact essential for activity. We have found that it can be replaced by a 2-naphthylsulphonamido group, or by certain other arylsulphonamido groups. Also, we have found that certain 2-naphthylsulphonamido compounds and analogues possess antagonist activity at the gastrin receptor, in addition to (or instead of) activity at the CCK receptor.

A number of such 2-naphthylsulphonamido compounds and analogues are disclosed in our co-pending International Patent Application No. PCT/GB91/01111. These compounds are of the formula

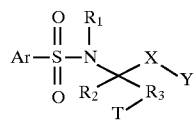

in which Ar is 2-naphthyl, 2-naphthylmethyl, 2-(1,2,3,4-tetrahydronaphthyl), phenethyl, styryl, indanyl (or a substituted derivative of any of the foregoing), or 3,4-dichlorophenyl; $R_1$ is H. $C_1$ to $C_6$ alkyl, $C_1$ to $C_6$ alkenyl, cycloalkyl, —$(CH_2)_q$aryl, —$(CH_2)_q$(substituted aryl) or —$(CH_2)_q$heterocyclic, wherein q is 0 to 4; $R_2$ is H, methyl or ethyl; $R_3$ is —$(CH_2)_n$—(wherein n is from 0 to 3); X is —C(O)—; T is carboxyl, —$CONR_4R_5$ (wherein $R_4$ and $R_5$ are independently H or $C_1$ to $C_4$ alkyl) or tetrazolyl; and Y is

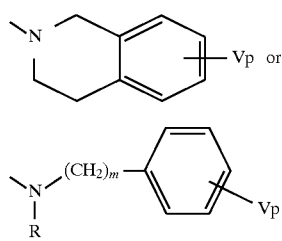

wherein
R is H. $C_1$ to $C_5$ alkyl, —$(CH_2)_r$-aryl or —$(CH_2)_r$-substituted aryl, r being from 0 to 4, V is $C_1$ to $C_4$ alkyl, $C_1$ to $C_4$ alkoxy, $C_1$ to $C_4$ alkylthio, carboxy, $C_1$ to $C_4$ carboalkoxy, nitro, trihalomethyl, hydroxy, —NR'R" (R' and R" being independently H or $C_1$ to $C_4$ alkyl), $C_1$ to $C_4$ alkylaryl, $C_1$ to $C_4$ alkyl (substituted aryl) or halo, m is 1 to 3 and p is 0 to 3.

PCT/GB91/01111 also discloses that the corresponding 1-naphthyl compounds are inactive.

According to the present invention, there is provided a method of counteracting a physiological effect of cholecystokinin or gastrin in a patient, comprising administering to said patient an effective amount of a compound of the formula

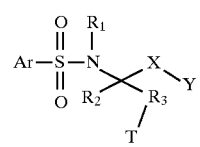

wherein Ar is naphthyl, naphthylmethyl, 1,2,3,4-tetrahydronaphthyl, phenethyl, styryl, indanyl or substituted derivatives of any of the foregoing, or 3,4-dichlorophenyl, $R_1$ is H, $C_1$ to $C_6$ alkyl, $C_1$ to $C_6$ alkenyl, cycloalkyl, —$(CH_2)_q$aryl, —$(CH_2)_q$(substituted aryl), —$(CH_2)_q$heterocyclic or —$(CH_2)_q$(substituted heterocyclic), wherein q is 0 to 4, $R_2$ is H, methyl or ethyl, $R_3$ is $C_1$ to $C_3$ alkylene or is absent, T is carboxyl, —$CONR_4R_5$ (wherein $R_4$ and $R_5$ are independently H or $C_1$ to $C_4$ alkyl), —$COOR_{13}$ (wherein $R_{13}$ is $C_1$ to $C_4$ alkyl, benzyl or substituted benzyl) or tetrazolyl, X is —C(O)— or —$CH_2$—, and Y is —$NR_6R_7$ or —O—$R_6$ (wherein $R_6$ and $R_7$ are independently H, $C_1$ to $C_{15}$ hydrocarbyl or halo-substituted $C_1$ to $C_{15}$ hydrocarbyl in which up to 6 carbon atoms may be replaced by —O—, —S—, or —$NR_8$— ($R_8$ being absent or selected from H, $C_1$ to $C_{12}$ hydrocarbyl, $C_1$ to $C_{12}$ hydrocarbylcarbonyl and $C_1$ to $C_{12}$ hydrocarbyloxycarbonyl), provided that neither $R_6$ nor $R_7$ contains a —O—O— group, and wherein $R_6$ and $R_7$ may be linked by a single or double bond), or a pharmaceutically acceptable salt thereof, provided that when a) $R_3$ is —$(CH_2)_n$— (wherein n is from 0 to 3); b) X is —C(O)—; c) $R_1$ is not —$(CH_2)_q$(substituted heterocyclic); and d) Y is

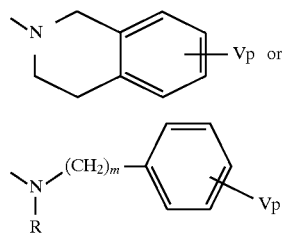

(wherein

R is H, $C_1$ to $C_5$ alkyl, —$(CH_2)_r$-aryl or —$(CH_2)_r$-substituted aryl, r being from 0 to 4, V is $C_1$ to $C_4$ alkyl, $C_1$ to $C_4$ alkoxy, $C_1$ to $C_4$ alkylthio, carboxy, $C_1$ to $C_4$ carboalkoxy, nitro, trihalomethyl, hydroxy, —$NR_9R_{10}$ ($R_9$ and $R_{10}$ being independently H or $C_1$ to $C_4$ alkyl), $C_1$ to $C_4$ alkylaryl, $C_1$ to $C_4$ alkyl (substituted aryl) or halo, m is 1 to 3, and p is 0 to 3)

then T is —$COOR_{13}$ and Ar is not 1-naphthyl, 1-naphthylmethyl or 1-(1,2,3,4-tetrahydronaphthyl).

Certain compounds according to formula II in which Ar is 3,4-dichlorophenyl are disclosed by Jha et al, Indian Journal of Chemistry 26B, 542–545 (1987); De et al, Indian J. Pharm. Sci. 47, 93–96 (1985); and Jha et al, Indian J. Pharm. Sci. 49(4), 133–136 (1987) as possible antineoplastic agents. 2-Naphthalenesulphonylserine is disclosed in EP-A-0236163 as an antithrombotic agent. Naphthyl-sulphonamidosuccinic acid and the disodium salt of the corresponding glutaric acid compound are disclosed by Bhatt et al, Indian Chemical Journal 13(3), 21–22 (1978) as antimicrobial agents. Accordingly, no claim is made herein to such compounds per se.

According to a further aspect of the present invention, therefore, there is provided a compound of formula II above, or a pharmaceutically acceptable salt thereof, provided that Ar is not 3,4-dichlorophenyl and that T is not carboxyl when X is —C(O)— and Y is —OH, and further provided that said compound is not 2-naphthalenesulphonyl-L-aspartyl (2-phenethyl)-amide.

The terms "hydrocarbyl" and "hydrocarbylene", as used herein, refer respectively to monovalent and divalent groups consisting of carbon and hydrogen. Hydrocarbyl groups thus include alkyl, alkenyl, alkynyl, cycloalkyl, cycloalkenyl, aryl, alkylaryl, alkenylaryl, alkynylaryl, cycloalkylaryl, and cycloalkenylaryl groups, in both straight and branched chain forms. A "carbocyclic" group, as the term is used herein, comprises one or more closed chains or rings, which consist entirely of carbon atoms. Included in such groups are alicyclic groups such as cyclopropyl, cyclobutyl, cyclopentyl, cyclohexyl and adamantyl, as well as aromatic groups such as phenyl, naphthyl, indanyl, fluorenyl, (1,2,3,4)-tetrahydronaphthyl, indenyl and isoindenyl. The term "aryl" is used herein to refer to aromatic carbocyclic groups, including those mentioned above.

A "heterocyclic" group comprises one or more closed chains or rings which have at least one atom other than carbon in the closed chain or ring. Examples include thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

When reference is made herein to a substituted aryl group (such as "substituted benzyl") or a substituted heterocyclic group, the substituents are preferably from 1 to 3 in number (and more usually 1 or 2 in number), and are preferably independently selected from $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl) amino, aryl, $C_1$ to $C_6$ alkylaryl, halo, sulphamoyl and cyano.

The term "halogen", as used herein, refers to any of fluorine, chlorine, bromine and iodine. Most usually, however, halogen substituents in the compounds of the invention are chlorine or fluorine substituents.

The term "carboalkoxy", as used herein, refers to a group of the form R—C(O)—O—, wherein R is H or alkyl.

Ar is preferably selected from 2-naphthyl, 2-naphthylmethyl, 2-(1,2,3,4-tetrahydronaphthyl), phenethyl, styryl, indanyl and substituted derivatives of any of the foregoing. If Ar is 1-naphthyl, 1-naphthylmethyl or 1-(1,2,3, 4-tetrahydronaphthyl), $R_6$ and $R_7$ are preferably aliphatic or cycloaliphatic groups.

Ar is preferably unsubstituted or has 1 or 2 substituents selected from halo, $C_1$ to $C_4$ alkyl, $C_1$ to $C_4$ alkoxy, sulphamoyl, trihalomethyl, nitro, carboxylate and nitrile.

Included in the definition of $R_6$ and $R_7$ are $C_1$ to $C_9$ alkyl, $C_1$ to $C_6$ alkoxy $C_1$ to $C_6$ alkyl, $C_1$ to $C_6$ alkylthio $C_1$ to $C_6$ alkyl, $C_1$ to $C_6$ alkylamino $C_1$ to $C_6$ alkyl, di($C_1$ to $C_4$ alkyl)amino $C_1$ to $C_6$ alkyl, $C_1$ to $C_9$ alkenyl, $C_1$ to $C_9$ alkynyl, $C_3$ to $C_9$ cycloalkyl, $C_4$ to $C_9$ cycloalkenyl, and saturated heterocyclic groups containing one, two or three ring heteroatoms, all of which groups may optionally have halogen substituents. Also included are aryl, $C_1$ to $C_6$ alkylaryl, $C_1$ to $C_6$ alkenylaryl, $C_1$ to $C_6$ alkynylaryl, $C_3$ to $C_6$ cycloalkylaryl, and $C_4$ to $C_6$ cycloalkenylaryl groups, as well as heterocyclic analogues thereof having one, two or three ring heteroatoms, and mono-, di- and tri-substituted derivatives wherein the substituents are independently selected from $C_1$ to $C_4$ alkyl, $C_1$ to $C_4$ alkoxy, $C_1$ to $C_4$ alkylthio, carboxy, $C_1$ to $C_4$ carboalkoxy, nitro, trihalomethyl, hydroxy, —$NR_{11}R_{12}$(wherein $R_{11}$ and $R_{12}$ are independently H or $C_1$ to $C_4$ alkyl), $C_1$ to $C_4$ alkylaryl, and halo.

When $R_6$ and $R_7$ are linked, they may form a saturated or an unsaturated ring. In the case of aromatic rings, such may optionally be substituted as described above.

In preferred compounds according to the invention, $R_6$ and $R_7$ are both saturated groups or are linked to form a saturated carbocyclic or heterocyclic group. When heteroatoms are present in $R_6$ and/or $R_7$, they are preferably up to 3 in number, and are preferably oxygen.

Particularly preferred groups for $R_6$ and $R_7$ include hydrogen, and methyl, ethyl, propyl, butyl, pentyl, hexyl, 3,3-dimethylbutyl, 3-methoxypropyl, 1-pentylhexyl, 1-ethyl-pentyl, 2-ethylhexyl, 2-cyclohexylethyl, 2-(1-adamantyl)ethyl, (1-adamantyl)methyl, and cyclododecyl groups. Examples of Y groups in which $R_6$ and $R_7$ are linked include 3-azaspiro[5.4]decylamino, 1,4-dioxa-8-azaspiro [5.4]decylamino, and 3-azabicyclo[3.2.2]nonylamino groups.

Preferably, T is selected from carboxyl and —$CONR_4R_5$, wherein $R_4$ and $R_5$ are as defined above.

Pharmaceutically acceptable salts of the acidic compounds of the invention include salts with alkali metals and alkaline earth metals, such as sodium, potassium, calcium and magnesium, and salts with organic bases. Suitable organic bases include amines such as N-methyl-D-glucamine.

Pharmaceutically acceptable salts of the basic compounds of the invention include salts derived from organic or inorganic acids. Suitable acids include hydrochloric acid, phosphoric acid, oxalic acid, maleic acid, succinic acid and citric acid.

The compounds of the invention have a chiral center at the carbon atom to which $R_2$ is attached. The present invention comprehends both the L- and the D- isomers of the compounds of formula I, as well as mixtures (eg. racemic mixtures) thereof.

The compounds of the invention in which T is a carboxyl or amido group, X is —C(O)— and Y is —$NR_6R_7$ may be prepared as shown in reaction scheme A. It will be noted that the reaction scheme illustrates the preparation of compounds in the L configuration, but exactly analogous methods are applicable to the preparation of the D or DL compounds.

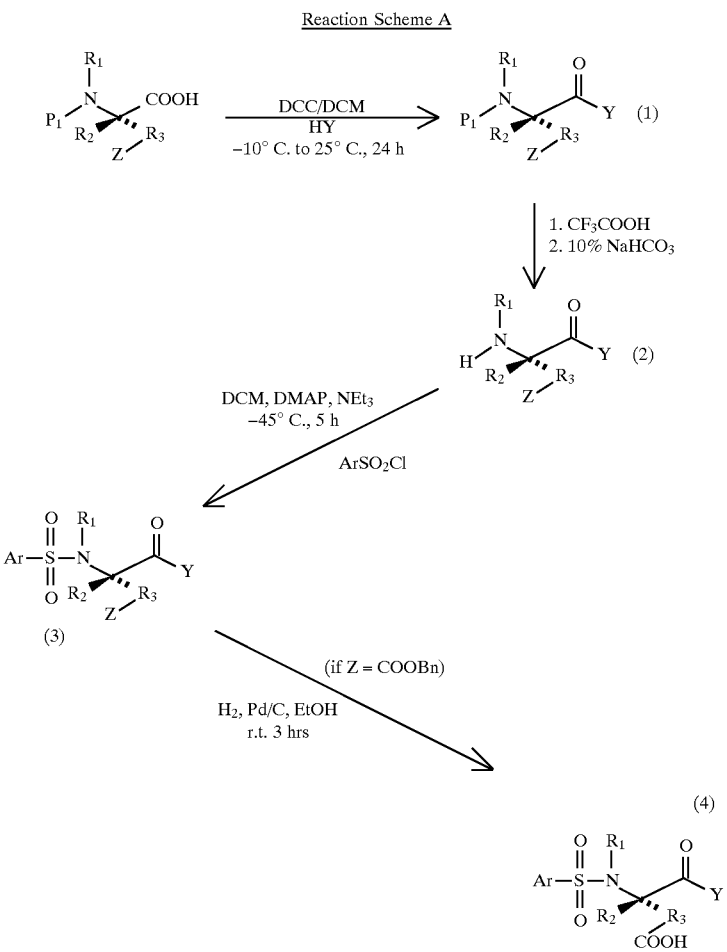

Reaction Scheme A

In reaction Scheme A, $R_1$, $R_2$ and $R_3$ have the meanings indicated above in relation to Formula II, while $P_1$ indicates an N-protecting group such as a t-butyloxycarbonyl, benzyloxycarbonyl, sulphonyl, acetyl, pivaloyl or aminoacyl group, and Z is a suitably protected carboxyl group or an amido group.

The first reaction in the scheme involves coupling an N-protected amino acid ester (such as an alkyl, benzyl or substituted benzyl ester) with a primary or secondary amine using a suitable peptide coupling reagent such as dicyclohexylcarbodiimide (DCC), bis(2-oxo-3-oxazolidinyl) phosphinic chloride, isobutyl chloroformate, phosphorus pentachloride, benzotriazol-1-yloxytris(dimethylamino) phosphonium hexafluorophosphate (BOP), benzotriazol-1-yloxytris (pyrrolidino)phosphonium hexafluorophosphate (PyBOP) or via the N-hydroxysuccinimide ester. The reaction conveniently takes place at a temperature of from −10° C. to 25° C. in a suitable solvent such as dichloromethane.

The protecting group $P_1$ is removed from the resulting amide (1) by standard methods. For example, if $P_1$ is a t-butyloxycarbonyl group, trifluoroacetic acid may conveniently be used, followed by neutralisation with sodium bicarbonate, to yield the corresponding amine (2). This is then reacted with the desired arylsulphonyl chloride in the presence of a base (preferably a tertiary amine such as triethylamine) and DMAP, to yield the sulphonamide (3).

If $R_3$ is present, and Z is a protected carboxyl group, it is then deprotected by suitable methods, to give the free acid form (4). When Z is a carboxyl group which is protected by means of its benzyl ester, it may conveniently be deprotected by catalytic hydrogenation (eg. over Pd/C), but it will be apparent that other methods could also be used.

Those compounds of formula I in which T is tetrazolyl may be made as shown in the following Reaction Scheme B.

Reaction Scheme B

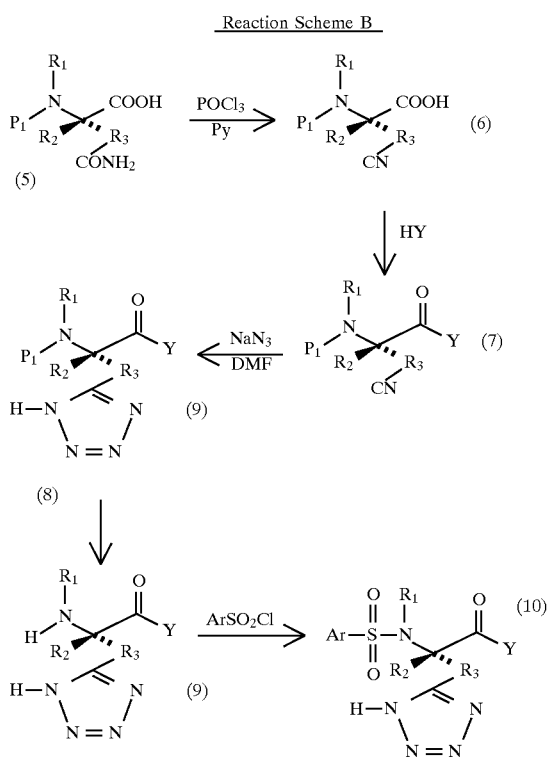

In this scheme, the N-protected asparagine analogue (5) is converted to the corresponding nitrile (6) by reaction with, for example, phosphorus oxychloride and pyridine. This is then coupled with the desired primary or secondary amine, using any of the coupling agents mentioned above, to yield compound (7). The latter is then converted to the tetrazole (8) by reaction with sodium azide in dimethylformamide, followed by deprotection of the amino-nitrogen using standard methods. The product (9) is finally reacted with the appropriate arylsulphonyl chloride to give the desired compound (10).

The compounds in which Y is —O—$R_6$ may be prepared by analogous routes, except that the ester linkage is formed by reacting the appropriate carboxylate salt (eg. the caesium salt) with a compound of the formula Br-$R_6$, in accordance with well known procedures. (See, for example, S. S. Wang et al, J. Org. Chem. (1977) 42, page 1286.) Alternatively, the compounds can be obtained by reacting an N-protected amino acid ester (such as an alkyl, benzyl or substituted benzyl ester) with the appropriate alcohol using a suitable peptide coupling reagent.

Also, the analogues in which X is —$CH_2$— may be prepared by methods which are analogous to those described by Martinez (J. Med. Chem., 30, 1366 (1987)). The appropriately protected amino acid is reduced to the corresponding aldehyde, which is then allowed to condense with the free amino group of a compound of the formula $HNR_6R_7$. The resulting Schiff base is then reduced using sodium cyanoborohydride.

Compounds in which X is —$CH_2$— and Y is —O—$R_6$ may be formed by further reduction of the aldehyde to the corresponding alcohol, and reaction of the anionic form of the alcohol (ie. in the presence of a strong base) with a compound of the formula Br-$R_6$. Alternatively, the alcohol may be activated (eg. by tosylation) and then reacted with a compound of the formula $^-O$—$R_6$.

An alternative method for the synthesis of certain compounds according to the invention is shown below in reaction scheme C.

Reaction Scheme C

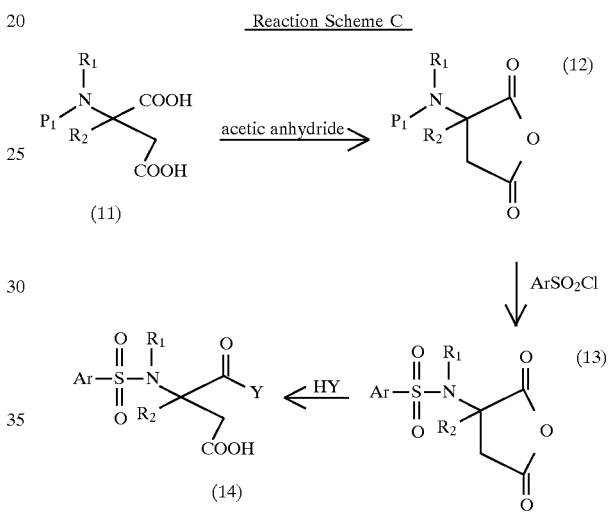

The N-protected amino acid (11) is reacted with a dehydrating agent such as acetic anhydride to form (12), which is deprotected and reacted with the appropriate arylsulphonyl chloride under the usual conditions to give the corresponding sulphonamide (13). Reaction with a primary or secondary amine affords the desired compound (14).

A still further method of preparation of the compounds of the invention is set out schematically in reaction scheme D.

Reaction Scheme D

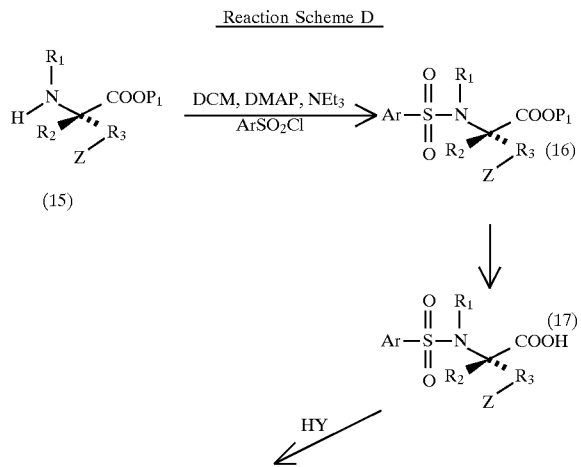

-continued
Reaction Scheme D

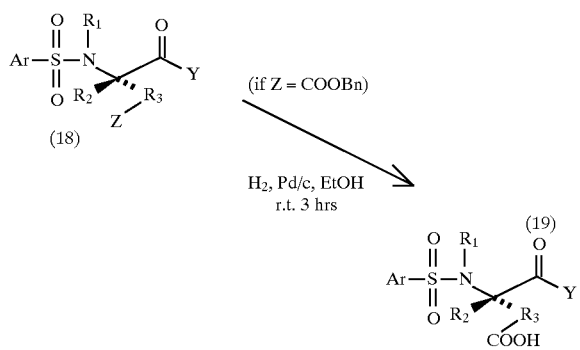

The first reaction in the scheme involves sulphonylation of the protected amino acid derivative (15) with the desired arylsulphonyl chloride. The product (16) is then deprotected by suitable methods. For example, if $P_1$ is an allyl group, it may be removed by an allyl transfer reaction in the presence of tetrakis (triphenylphosphine)palladium. Alternatively, $P_1$ may be phthalamidomethyl, which can be removed with hydrazine.

The free acid (17) is then reacted with a primary or secondary amine using a suitable peptide coupling reagent such as dicyclohexylcarbodiimide, bis (2-oxo-3-oxazolidinyl)phosphinic chloride, isobutyl chloroformate, phosphorus pentachloride, benzotriazol-1-yloxytris (dimethylamino)phosphonium hexafluorophosphate or via the N-hydroxysuccinimide ester. When Z is a protected carboxyl group, it may then be deprotected as described above in connection with reaction scheme A.

The present invention thus also provides a method of making a compound of formula II above, which method comprises the step of reacting a suitable protected compound of the formula

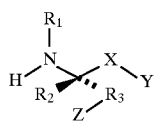

with a compound of the formula $ArSO_2Cl$ in the presence of a base, wherein Z is a protected carboxyl group, —$CONR_4R_5$ (wherein $R_4$ and $R_5$ are as defined above) or a tetrazolyl group.

The invention further provides a method of making a compound according to formula II wherein X is —C(O)—, which method comprises the step of reacting a compound of the formula

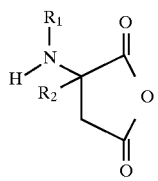

with a compound of the formula HY.

In a still further aspect, the invention provides a method of making a compound according to formula II, which method comprises the step of reacting a compound of the formula

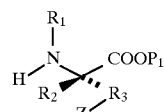

with a compound of the formula $ArSO_2Cl$ in the presence of a base, wherein Z is as defined above and $P_1$ is a protecting group.

Pharmaceutically acceptable salts of the acid or basic compounds of the invention can of course be made by conventional procedures, such as by reacting the free base or acid with at least a stoichiometric amount of the desired salt-forming acid or base.

The compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride.

Aqueous suspensions according to the invention may include suspending agents such as cellulose derivatives, sodium alginate, polyvinyl-pyrrolidone and gum tragacanth, and a wetting agent such as lecithin.

Suitable preservatives for aqueous suspensions include ethyl and n-propyl p-hydroxybenzoate.

The invention is now further illustrated by means of the following examples.

EXAMPLE 1

N-tert-Butyloxycarbonyl β-benzyl-L-aspartyl dipentylamide(1—1)

Dipentylamine (0.75 ml; 3.7 mmol) was added to N-tert-butyloxycarbonyl β-benzyl-L-aspartic acid N-hydroxysuccinimide ester (1.56 g; 3.72 mmol) and triethylamine (0.52 ml; 3.73 mmol) in dry DME (30 ml). The reaction mixture was stirred at room temperature for 16 hours under argon then evaporated to dryness. The residue was dissolved in ethyl acetate (40 ml), washed successively with 10% citric acid solution (40 ml), saturated sodium bicarbonate solution (40 ml), brine (2×40 ml) and dried (Na$_2$SO$_4$). Filtration and evaporation of the solvent afforded the product as a colorless oil.

yield (1.65 g; 96%)

β-Benzyl-L-aspartyl dipentylamide. (1—2)

N-tert-Butyloxycarbonyl β-benzyl-L-aspartyl dipentylamide (1—1) (0.88 g; 1.9 mmol) in trifluoroacetic acid (10 ml) was stirred at room temperature for 1 hour. The reaction mixture was evaporated to dryness and the resultant oil dissolved in DCM (30 ml), washed successively with saturated sodium bicarbonate solution (2×20 ml), brine (3×20 ml) and dried (Na$_2$SO$_4$). Filtration and evaporation of the solvent gave the product as a yellow oil which was used without further purification.

Yield (0.67 g; 97%)

2-Naphthalenesulphonyl-β-benzyl-L-aspartyl dipentylamide(1—3)

2-Napthtalenesulphonyl chloride (0.38 g; 1.7 mmol) triethylamine (0.23 ml); 1.7 mmol), DMAP (3 mg), and β-benzyl-L-aspartyl dipentylamide (1—2) (0.61 g; 1.7 mmol) were stirred in dry DCM (18 ml) under argon at −45° C. The reaction mixture was allowed to warm to room temperature over 3 hours, diluted with DCM (30 ml), washed with 10% citric acid solution (30 ml), saturated sodium bicarbonate solution (30 ml), brine (3×30 ml), and dried (Na$_2$SO$_4$). Filtration and evaporation of the solvent gave the crude product as an amorphous solid which was chromatographed on silica gel with acetone-toluene (1:20) as eluant. The product was obtained as a white amorphous solid.

Yield (0.68 g; 73%)

2-Naphthalenesulphonyl-L-aspartyl dipentylamide (1—4)

2-Naphthalenesulphonyl-β-benzyl-L-aspartyl dipentylamide (1—3) (0.54 g; 0.98 mmol) and 10% palladium on charcoal (72 mg) were stirred in ethanol (50 ml) under hydrogen at room temperature for 60 hours. The reaction mixture was passed through a pad of celite and evaporation of the filtrate afforded the product as a white solid, which was triturated with hexane.

Yield (0.45 g; 99%)

m.pt. 125°–126° C.

$[\alpha]^D = -13.3°$ (c=0.75%, MeOH)

Found C 61.33, H 7.44, N 6.01%; C$_{24}$H$_{34}$N$_2$O$_5$S +0.5H$_2$O requires C 61.12, H 7.48, N 5.94%:

EXAMPLE 2

2-Naphthalenesulphonyl D-glutamyl dipentylamide

The compound was prepared as in Example 1 except that N-tert-butyloxycarbonyl γ-benzyl-D-glutamic acid was used in place of N-tert-butyloxycarbonyl β-benzyl-L-aspartic acid N-hydroxysuccinimide ester in step (1—1).

m.pt 148° C.

$[\alpha]^D = -13.1°$ (c=0.25%, MeOH)

Found C 63.04, H 7.66, N 6.0%; C$_{25}$H$_{36}$N$_2$O$_5$S requires C 63.00, H 7.61, N 5.88%:

EXAMPLE 3

N-t-Butyloxycarbonyl β-benzyl-L-aspartic acid allyl ester(3—1)

Caesium carbonate (2.97 g; 9.12 mmole) and N-t-butyloxy-carbonyl-β-benzyl-L-aspartic acid (4.13 g; 12.8 mmol) in a 10:1 mixture of methanol and water (44 ml) were stirred at room temperature for 20 min and evaporated to dryness. The residue was re-evaporated from DMF (30 ml) and the resultant oil was stirred in DMF (40 ml) with allyl bromide (1.1 ml; 12.7 mmol) at room temperature for 17 h. The precipitated solid was removed by filtration and the filtrate was washed successively with 10% citric acid solution (30 ml), saturated sodium bicarbonate solution (30 ml) and brine (30 ml×2) and dried (sodium sulphate). Filtration and evaporation of the solvent gave the product as a yellow oil which was used without further purification.

Yield (4.5 g, 97%

β-Benzyl-L-aspartic acid allyl ester (3–2)

N-t-Butyloxycarbonyl β-benzyl-L-aspartic acid allyl ester (3–1) (2.95 g; 8.11 mmol) was stirred in trifluoracetic acid (30 ml) at room temperature for 45 min. The solvent was removed in vacuo and the residue evaporated from ether (30 ml×2). The resultant yellow oil was dissolved in DCM (40 ml), washed with saturated sodium bicarbonate solution (30 ml), brine (30 ml×2) and dried (sodium sulphate). Filtration and evaporation of the solvent gave the product as a yellow oil which was used without further purification.

Yield (2.01 g, 94%)

2-Naphthalenesulphonyl β-benzyl-L-aspartic acid allyl ester(3—3)

2-Naphthalenesulphonyl chloride (1.7 g; 7.5 mmol) was added to a solution of β-benzyl-L-aspartic acid allyl ester (3–2) (1.94 g; 7.4 mmol), triethylamine (1.1 ml; 7.6 mmol) and DMAP (10 mg) in dry DCM (40 ml) at −45° C. under argon. The reaction mixture was allowed to warm to room temperature over 30 min and stirred for a further 16 h. The solution was then washed successively with 10% citric acid solution (30 ml), saturated sodium bicarbonate solution (30 ml) and brine (30 ml ×2) and dried (sodium sulphate). Filtration and evaporation of the solvent gave the crude product as an oil which was purified by flash chromatography on silica gel with acetone-toluene (1:20 to 1:15) as eluant. The product was obtained as a colorless oil which solidified on standing.

Yield (3.03 g, 91%)

2-Naphthalenesulphonyl β-benzyl-L-aspartic acid (3—4)

Morpholine (3.3 ml; 38 mmol) was added to a solution of 2-Naphthalenesulphonyl β-benzyl-L-aspartic acid allyl ester (3—3) (1.73 g; 3.8 mmol) and tetrakis (triphenylphosphine) palladium (0.42 g; 0.37 mmol) in dry THF (40 ml) under an atmosphere of argon. The reaction mixture was stirred at room temperature for 2 h and then evaporated to dryness. The resultant yellow oil was triturated with ethyl acetate followed by filtration of the white solid obtained. The crude product was dissolved in DCM (30 ml) and then washed successively with 2N HCl (30 ml) and brine (30 ml×3). The solution was dried (sodium sulphate). Filtration and evaporation of the solvent gave the product as a white solid.

Yield (810 mg, 52%)

2-Naphthalenesulphonyl β-benzyl-L-aspartyl dibutylamide(3—5)

2-Naphthalenesulphonyl β-benzyl-L-aspartic acid (3—4) (179 mg; 0.43 mmol), dibutylamine (0.08 ml; 0.47 mmol), diisopropylethylamine (0.15 ml; 0.86 mmol), and PyBOP (236 mg; 0.45 mmol) were stirred in dry DCM (10 ml) for 14 h at room temperature. The reaction mixture was diluted with DCM (20 ml) washed successively with 5% potassium bisulphate solution (20 ml×2), saturated sodium bicarbonate (20 ml×2) and brine (30 ml×3). The solution was then dried (sodium sulphate). Filtration and evaporation of the solvent gave the product as a yellow oil, which was purified by chromatography on silica gel with acetone-toluene (1:5) as eluant to give the product as a colorless oil.

Yield (194 mg, 87%)

2-Naphthalenesulphonyl-L-aspartyl dibutylamide (3—6)

The compound was prepared essentially as described in example (1—4) except that 2-naphthalenesulphonyl β-benzyl-L-aspartyl dibutylamide (3—5) was used in place of 2-naphthalenesulphonyl β-benzyl-L-aspartyl dipentylamide (1—3). m.pt 62°–65° C. $[\alpha]^D=-16.6°$ (c=0.71%, MeOH)

Found C 60.87, H 7.08, N 6.25%; $C_{22}H_{30}N_2O_5S$ requires C 60.81, H 6.96, N 6.45%:

EXAMPLE 4

2-Naphthalenesulphonyl-L-aspartyl dihexylamide

The compound was prepared as in Example 3 except that dihexylamine was used in place of dibutylamine in step (3—5). $[\alpha]^D=-13.8°$ (c=0.57%, MeOH). Found C 62.64, H 7.91, N 5.56%; $C_{26}H_{38}N_2O_5S$. $0.5H_2O$ requires C 62.50, H 7.87, N 5.61%:

EXAMPLE 5

2-Naphthalenesulphonyl-L-aspartyl pentylamide

The compound was prepared as in Example 3 except that pentylamine was used in place of dibutylamine in step (3—5). m.pt 160–163° C. $[\alpha]^D=-15.3°$ (c=0.99%, MeOH). Found C 58.01, H 6.17, N 6.77%; $C_{19}H_{24}N_2O_5S$ requires C 58.15, H 6.16, N 7.15%:

EXAMPLE 6

2-Naphthalenesulphonyl-L-aspartyl (3,3-dimethyl)-butylamide

The compound was prepared as in Example 3 except that 3,3-dimethylbutylamine was used in place of dibutylamine in step (3—5). m.pt 188°–190° C. $[\alpha]^D=-14.0°$ (c=0.5%, MeOH).

Found C 59.02, H 6.48, N 7.07%; $C_{20}H_{26}N_2O_5S$ requires C 59.10, H 6.45, N 6.89%:

EXAMPLE 7

2-Naphthalenesulphonyl-L-aspartyl N-(methyl) hexylamide

The compound was prepared as in Example 3 except that N-methylhexylamine was used in place of dibutylamine in step (3—5). m.pt 54°–57° C. $[\alpha]^D=-33.6°$ (c=0.55%, MeOH). Found C 55.95, H 6.86, N 6.11%; $C_{21}H_{28}N_2O_5S$. $1.5H_2O$ requires C 56.36, H 6.98, N 6.26%:

EXAMPLE 8

2-Naphthalenesulphonyl-L-aspartyl N-(3-methoxypropyl)pentylamide

The compound was prepared as in Example 3 except that N-(3-methoxypropyl)pentylamine was used in place of dibutylamine in step (3—5). m.pt 111°–114° C. $[\alpha]^D=-16.2°$ (c=0.52%, MeOH). Found C 58.58, H 7.23, N 6.05%; $C_{23}H_{32}N_2O_5S$. $0.5H_2O$ requires C 58.33, H 7.02, N 5.92%:

EXAMPLE 9

2-Naphthalenesulphonyl-L-aspartyl (1-pentyl) hexylamide

The compound was prepared as in Example 3 except that 6-aminoundecane was used in place of dibutylamine in step (3—5). m.pt 118°–121° C. $[\alpha]^D=-8.6°$ (c=1.0%, MeOH). Found C 61.85, H 7.65, N 5.65%; $C_{25}H_{36}N_2O_5S$ requires C 62.00, H 7.61, N 5.88%:

EXAMPLE 10

2-Naphthalenesulphonyl-L-aspartyl 1-adamantylmethylamide

The compound was prepared as in Example 3 except that 1-adamantylmethylamine was used in place of dibutylamine in step (3—5). $[\alpha]^D=-20.5°$ (c=0.55%, MeOH). Found C 62.85, H 6.87, N 5.41%; $C_{25}H_{30}N_2O_5S$. EtOH requires C 62.77, H 7.02, N 5.42%:

EXAMPLE 11

2-Naphthalenesulphonyl-L-aspartyl 2-cyclohexylethylamide

The compound was prepared as in Example 3 except that 2-cyclohexylethylamine was used in place of dibutylamine in step (3—5). m.pt 166°–168° C. $[\alpha]^D=-15.6°$ (c=0.41%, MeOH). Found C 60.09, H 6.57, N 6.32%; $C_{22}H_{28}N_2O_5S$. $0.5H_2O$ requires C 59.85, H 6.62, N 6.34%:

EXAMPLE 12

2-Naphthalenesulphonyl-L-aspartyl 2-(1-adamantyl) ethylamide

The compound was prepared as in Example 3 except that 2-(1-adamantyl)ethylamine was used in place of dibutylamine in step (3—5). m.pt 116°–118° C. $[\alpha]^D=-16.7°$ (c=1.03%, MeOH).

Found C 61.87, H 6.86, N 5.58%; $C_{26}H_{32}N_2O_5S$. $H_2O$ requires C 62.13, H 6.82, N 5.57%:

EXAMPLE 13

2-Naphthalenesulphonyl-L-aspartyl 3-azaspiro[5.4] decylamide

The compound was prepared as in Example 3 except that 3-azaspiro[5.4]decane was used in place of dibutylamine in step (3—5). m.pt 129°–130° C. $[\alpha]^D=+5.6°$ (c=0.54%, MeOH).

Found C 61.92, H 6.51, N 6.17%; $C_{23}H_{28}N_2O_5S$ requires C 62.14, H 6.35, N 6.30%:

EXAMPLE 14

2-Naphthalenesulphonyl-L-aspartyl 1,4-dioxa-8-azaspiro-[5.4]decylamide

The compound was prepared as in Example 3 except that 1,4-dioxa-8-azaspiro[5.4]decane was used in place of dibutylamine in step (3—5). m.pt 188°–189° C. $[\alpha]^D=-14.0°$ (c=0.4%, MeOH). Found C 56.13, H 5.22, N 6.00%; $C_{21}H_{24}N_2O_7S$ requires C 56.24, H 5.39, N 6.25%:

EXAMPLE 15

2-Naphthalenesulphonyl-L-aspartyl 3-azabicyclo-[3.2.2]nonylamide

The compound was prepared as in Example 3 except that 3-azabicyclo[3.2.2]nonane was used in place of dibutylamine in step (3—5). m.pt 82°–85° C. $[\alpha]^D = -24.4°$ (c=0.5%, MeOH).

Found C 59.87, H 6.11, N 6.05%; $C_{22}H_{26}N_2O_5S$. 0.75$H_2O$ requires C 59.51, H 6.24, N 6.31%:

EXAMPLE 16

2-Naphthalenesulphonyl-L-aspartyl cyclododecylamide

The compound was prepared as in Example 3 except that cyclododecylamine was used in place of dibutylamine in step (3—5). m.pt 190°–192° C. $[\alpha]^D = -20.5°$ (c=0.55%, MeOH).

Found C 62.20, H 8.11, N 4.97%; $C_{26}H_{36}N_2O_5S$. 1.5EtOH requires C 62.45, H 8.13, N 5.02%:

EXAMPLE 17

2-Naphthalenesulphonyl-L-aspartyl di(2-ethyl)hexylamide

The compound was prepared as in Example 3 except that di(2-ethyl)hexylamine was used in place of dibutylamine in step (3—5). $[\alpha]^D = -18.5°$ (c=0.71%, MeOH). C 64.53, H 8.37, N 5.07% $C_{30}H_{46}N_2O_5S$. 0.5$H_2O$ requires C 64.83, H 8.52, N 5.04%:

EXAMPLE 18

2-Naphthalenesulphonyl-D-aspartyl dipentylamide

The compound was prepared as in Example 1 except that N-tert-butyloxycarbonyl β-benzyl-D-aspartic acid was used in place of N-tert-butyloxylcarbonyl β-benzyl-L-aspartic acid N-hydroxysuccinimide ester in step (1—1). m.pt 122° C. $[\alpha]^D = +11.5°$ (c=1.0%, MeOH). Found C 61.52, H 7.34, N 6.00%; $C_{24}H_{34}N_2O_5S$. 0.25$H_2O$ requires C 61.68, H 7.46, N 5.99%:

EXAMPLE 19

2-Naphthalenesulphonyl-L-glutamyl dipentylamide

The compound was prepared as in Example 1 except that N-tert-butyloxycarbonyl γ-benzyl-L-glutamic acid was used in place of N-tert-butyloxylcarbonyl β-benzyl-L-aspartic acid N-hydroxysuccinimide ester in step (1—1). m.pt 140°–145° C. $[\alpha]^D = +29.2°$ (c=1.0%, MeOH). Found C 62.06, H 7.62, N 5.92%; $C_{25}H_{36}N_2O_5S$ requires C 62.00, H 7.61, N 5.88%:

EXAMPLE 20

2-Naphthalenesulphonyl-L-aspartyl pentyl ester

The compound was prepared as in example 3 except that 1-pentanol was used in place of dibutylamine in step (3—5). m.pt 94°–95° C. $[\alpha]^D = -16.2°$ (c=0.52%, MeOH). Found C 57.83, H 5.61, N 3.76%; $C_{19}H_{23}NO_6S$ requires C 58.00, H 5.89, N 3.56%:

EXAMPLE 21

1-Naphthalenesulphonyl-L-aspartyl dipentylamide

The compound was prepared as in example 1 except that 1-naphthalenesulphonyl chloride was used in place of 2-naphthalenesulphonyl chloride in step (1—3). m.pt 95°–98° C. $[\alpha]^D = -24.1°$ (c=1.0%, MeOH). Found C 61.60, H 7.38, N 6.00%; $C_{24}H_{34}N_2O_5S$. 0.25$H_2O$ requires C 61.68, H 7.46, N 5.99%:

$^1$H NMR data for the compounds disclosed in the examples are as follows:

Ex.1—1 $\delta_H$(300 MHz; CDCl$_3$) 7.4(5H,s) 5.35(1H,d) 5.15(2H,s) 5.0(1H,q) 3.35(4H,2×m) 2.8(2H,2×dd) 1.5(4H,m) 1.4(9H,s) 1.3(8H,m) 0.9(6H,2×t)

Ex.1—2 $\delta_H$(300 MHz; CDCl$_3$) 7.4(5H,s) 5.2(2H,s) 4.1(1H,s) 3.3(4H,m) 2.7(2H,2×dd) 1.7(2H,bs) 1.6(4H,m) 1.3(8H,m) 0.9(6H,m)

Ex.1—3 $\delta_H$(300 MHz; CDCl$_3$) 8.45(1H,s) 7.9(3H,m) 7.8(1H,d) 7.65(2H,m) 7.4(5H,m) 6.05(1H,d) 5.05(2H,s) 4.6(1H,q) 3.1(4H,m) 2.6(2H,d) 1.2(12H,m) 0.8(6H,m)

Ex.1—4 $\delta_H$(300 MHz; CDCl$_3$) 8.45(1H,s) 7.9(4H,m) 7.6(2H,m) 6.6(1H,bs) 4.7(1H,bs) 3.2(2H,m) 3.05(2H,t) 2.6(2H,2×dd) 1.3(12H,m) 0.8(6H,2×t)

Ex.2 $\delta_H$(300 MHz; CDCl$_3$) 8.45(1H,s) 7.9(4H,m) 7.6(2H,m) 6.35(1H,d) 4.2(1H,t) 3.2(1H,m) 3.0(4H,m) 2.6(1H,2×t) 1.9(1H,m) 1.7(1H,m) 1.0(12H,m) 0.8(6H,t)

Ex.3—1 $\delta_H$ (CDCl$_3$) 7.4(5H,m) 5.85(1H,m) 5.6(1H,d) 5.29(1H,dd) 5.24(1H,dd) 5.15(2H,s) 4.6(3H,m) 3.1(1H,dd) 2.9(1H,dd) 1.45(9H,s)

Ex.3—2 $\delta_H$ (CDCl$_3$) 7.3(5H,m) 5.9(1H,m) 5.3(1H,dd) 5.2(1H,dd) 5.15(2H,s) 4.6(2H,d) 3.85(1H,q) 2.8(2H,dd) 2.0(2H,bs)

Ex.3—3 $\delta_H$ (CDCl$_3$) 8.45(1H,s) 7.9(4H,m) 7.65(2H,m) 7.3(5H,m) 5.95(1H,d) 5.6(1H,m) 5.1(4H,m) 4.35(3H,m) 3.0(2H,2×dd)

Ex.3—4 $\delta_H$ (CDCl$_3$) 8.45(1H,s) 7.9(4H,m) 7.65(2H,m) 7.3(5H,m) 6.2(2H,bs) 5.0(2H,s) 4.2(1H,bs) 3.0(2H,2×dd)

Ex.3—6 $\delta_H$(500 MHz; DMSO-d$^6$) 8.4(1H,s) 8.1(2H,dd) 8.0(1H,d) 7.8(1H,dd) 7.65(2H,dt) 4.5(1H,t) 3.3(1H,m) 3.05(2H,m) 2.9(1H,m) 2.5(1H,dd) 2.05(1H,dd) 1.45(2H,t) 1.2(2H,q) 1.0(4H,m) 0.85(3H,t) 0.7(3H,t)

Ex.4 $\delta_H$(500 MHz; DMSO-d$^6$) 8.4(1H,s) 8.1(2H,dd) 8.0(1H,d) 7.8(1H,dd) 7.65(2H,dt) 4.45(1H,t) 3.3(1H,m) 3.0(2H,m) 2.85(1H,m) 2.55(1H,dd) 2.1(1H,dd) 1.45(2H,m) 1.2(8H,m) 1.05(6H,m) 0.85(6H,dt)

Ex.5 $\delta_H$(500 MHz; DMSO-d$^6$) 8.4(1H,s) 8.1(1H,d) 8.05(1H,d) 8.0(1H,d) 7.8(2H,m) 7.65(2H,m) 4.1(1H,t) 2.6(2H,2×m) 2.4(1H,dd) 2.3(1H,dd) 1.05(2H,m) 0.95(4H,m) 0.75(3H,t)

Ex.6 $\delta_H$(300 MHz; DMSO-d$^6$) 8.4(1H,s) 8.2(1H,bs) 8.05(3H,m) 7.8(1H,d) 7.7(3H,m) 4.05(1H,t) 2.6(2H,m) 2.4(2H,2×dd) 0.8(2H,m) 0.6(9H,s)

Ex.7 $\delta_H$(500 MHz; DMSO-d$^6$) 8.4(1H,2×s) 8.1(2H,d) 8.0(1H,t) 7.8(1H,d) 7.65(2H,m) 4.5(1H,2×t) 3.05 and 3.3(1H,m) 2.8(1H,t) 2.6(1H,2×dd)2.5 and 2.9(3H,2×s) 2.1(1H,2×dd) 1.4(1H,m) 1.15(4H,m) 1.0(3H,m) 0.8(3H,dt)

Ex.8 $\delta_H$(500 MHz; DMSO-d$^6$) 8.4(1H,2×s) 8.15(1H,d) 8.1(1H,dd) 8.0(1H,d) 7.8(1H,dd) 7.65(2H,dt) 4.5(1H,m) 3.75(2H,m) 3.1 and 3.2(3H,2×s) 3.0(4H,m) 2.5(1H,m) 2.1(1H,m) 1.7(1H,t) 1.45(1H,t) 1.35(1H,t) 1.2(1H,q) 1.1(4H,m) 0.8(3H,2×t)

Ex.9 $\delta_H$(500 MHz; DMSO-d$^6$) 8.4(1H,s) 8.15(1H,bs) 8.1(1H,d) 8.05(1H,d) 8.0(1H,d) 7.7(1H,dd) 7.65(2H,dt) 7.5(1H,d) 4.1(1H,bs) 3.3(1H,m) 2.5(1H,dd) 2.35(1H,dd) 1.15(4H,dd) 1.0(8H,m) 0.9(4H,m) 0.8(6H,m)

Ex.10 $\delta_H$(500 MHz; DMSO-d$^6$) 8.4(1H,s) 8.1(1H,d) 8.05(1H,d) 8.0(1H,d) 7.8(1H,dd) 7.65(3H,m) 4.15(1H,t) 2.5(2H,m) 2.35(2H,m) 1.75(3H,s) 1.5(6H,dd) 1.2(6H,s)

Ex.11 $\delta_H$(500 MHz; DMSO-d$^6$) 8.4(1H,s) 8.1(1H,d) 8.05 (1H,d) 8.0(1H,d) 7.8(2H,m) 7.65(2H,2×t) 4.1(1H,t) 2.6 (2×m) 2.4(1H,dd) 2.3(1H,dd) 1.55(3H,m) 1.4(2H,d) 1.1(3H,m) 1.0(1H,m) 0.9(2H,m) 0.6(2H,m)

Ex.12 $\delta_H$(500 MHz; DMSO-d$^6$) 8.4(1H,s) 8.1(1H,d) 8.05 (1H,d) 8.0(1H,d) 7.75(1H,dd) 7.65(3H,m) 4.05(1H,t) 2.5(2H,2×m) 2.45(1H,dd) 2.3(1H,dd) 1.8(3H,s) 1.55 (8H,dd) 1.2(6H,s) 0.7(2H,2×m)

Ex.13 $\delta_H$(300 MHz; CDCl$_3$) 8.45(1H,s) 8.2(1H,bs) 7.9 (4H,m) 7.6(2H,m) 6.7(1H.bs) 4.7(1H,m) 3.35(3H,m) 3.0(1H,m) 2.6(2H,m) 1.5(4H,s) 1.3(4H,s) 0.9(4H,m)

Ex.14 $\delta_H$(500 MHz; DMSO-d$^6$) 8.4(1H,s) 8.15(1H,d) 8.1(1H,d) 8.0(1H,d) 7.8(1H,dd) 7.65(2H,dt) 4.6(1H, dd) 3.85(4H,d) 3.45(2H,2×m) 3.15(2H,2×m) 2.6(1H, dd) 2.1(1H,dd) 1.55(2H,2×m) 1.3(1H,m) 1.2(1H,m)

Ex.15 $\delta_H$(500 MHz; DMSO-d$^6$) 8.45(1H,s) 8.35(1H,bs) 8.15(1H,d) 8.1(1H,d) 8.0(1H,d) 7.8(1H,dd) 7.7(2H,dt) 4.65(1H,t) 3.5(2H,2×dd) 3.35(1H,m) 3.15(1H,dd) 2.6 (1H,dd) 2.0(1H,dd) 1.8(2H,d) 1.6(1H,m) 1.5(3H,m) 1.4(2H,m) 1.3(2H,m) 1.15(1H,m)

Ex.16 $\delta_H$(500 MHz; DMSO-d$^6$) 8.4(1H,s) 8.15(1H,d) 8.1(1H,d) 8.05(1H,d) 8.0(1H,d) 7.8(1H,dd) 7.65(2H, dt) 7.5(1H,d) 4.35(1H,t) 4.1(1H,q) 3.45(2H,m) 3.3(2H, m) 2.5(1H,dd) 2.35(1H,dd) 1.2(14H,m) 0.95(1H,m) 0.85(2H,m) 0.65(1H,m)

Ex.17 $\delta_H$(500 MHz; DMSO-D$^6$) 8.4(1H,s) 8.1(2H,d) 8.0 (1H,d) 7.8(1H,dd) 7.65(2H,dt) 4.5(1H,m) 3.0(4H,m) 2.45(1H,m) 2.0(1H,m) 1.55(2H,m) 1.1(14H,m) 0.8 (8H,m) 0.75(6H,m)

Ex.18 $\delta_H$(500 MHz; CDCl$_3$) 9.2(1H,bs) 8.45(1H,s) 7.9 (2H,d) 7.85(2H,t) 7.55(2H,2×t) 6.75(1H,bs) 4.55(1H, bs) 3.15(2H,2×m) 3.0(2H,t) 2.55(2H,2×dd) 1.35(2H,m) 1.2(2H,t) 1.1(6H,m) 1.05(2H,m) 0.8(6H,2×t)

Ex.19 $\delta_H$(500 MHz; CDCl$_3$) 8.4(1H,s) 7.95(1H,d) 7.85 (1H,d) 7.7(2H,m) 7.55(2H,m) 6.5(1H,d) 4.2(1H,t) 3.15 (1H,m) 2.9(4H,m) 2.6(1H,dt) 1.9(1H,m) 1.55(1H,m) 1.05(6H,m) 0.9(6H,m) 0.75(6H,q)

Ex.20 $\delta_H$(500 MHz; DMSO-d$^6$) 8.5(1H,d) 8.4(1H,s) 8.15 (1H,d) 8.1(1H,d) 8.0(1H,d) 7.8(1H,dd) 7.65(2H,m) 4.2 (1H,q) 3.65(1H,dt) 3.5(1H,dt) 2.65(1H,dd) 2.5(1H,m) 1.15(2H,m) 1.05(2H,m) 0.95(2H,m) 0.75(3H,t)

Ex.21 $\delta_H$(500 MHz; CDCl$_3$) 8.6(1H,d) 8.3(1H,d) 8.05 (1H,d) 7.9(1H,d) 7.65(1H,t) 7.55(1H,t) 7.5(1H,t) 6.7 (1H,bs) 4.55(1H,t) 3.0(4H,2×m) 2.5(2H,2×dd) 1.35 (2H,m) 1.25(4H,m) 1.1(6H,m) 0.85(6H,2×t)

BIOLOGICAL DATA

The compounds of the examples were assayed using a CCK-receptor bioassay as follows:

Isolated, strip preparations were prepared from gall-bladders removed from male Dunkin-Hartley guinea-pigs (250–500 g body weight) according to the method of La Morte, W. W., et al., J.P.E.T., 217, (3), 638–644 (1981).

The complete gall-bladder is removed and opened along the longitudinal axis. Strips measuring 3 mm in the longitudinal axis and 1 mm in the transverse axis are cut and then tied with cotton to stainless steel wires. The preparation is connected to a GRASS FTO3 isometric transducer under an initial loading tension of 1 g and is immersed in 20 mls of Krebs solution maintained at 37° C. and gassed with 95% $O_2$/5% $CO_2$. The Krebs solution is as detailed above in connection with the fundus assay, except that the $Ca^{2+}$ concentration is decreased to 0.5 mM. After 30 mins the preparation is washed. Drug addition begins after an initial 90 min stabilisation period. Responses are measured as changes in tension from that immediately prior to any drug addition. Single cumulative agonist concentration-effect curves, using CCK-8 as agonist, are obtained on each preparation in the absence and presence of test compound which has been incubated for 60 minutes. The antagonist activity of the test compound is estimated and expressed as the negative logarithm (base 10) of the equilibrium dissociation constants ($pK_B$) using the modifications of standard competitive analysis described by Black et al., Br. J. Pharmacol.,86,571–579, (1985) and Shankley et al., Br. J. Pharmacol.,94,264–274 (1988). The results are set out in Table 1.

TABLE 1

| Example | $pK_B$ versus CCK (gallbladder) |
|---------|-------------------------------|
| 1 | 6.7 |
| 2 | 6.0 |
| 3 | 6.2 |
| 4 | 6.8 |
| 5 | 6.4 |
| 6 | 6.3 |
| 7 | 6.5 |
| 8 | 6.7 |
| 9 | 6.7 |
| 10 | 7.2 |
| 11 | 7.1 |
| 12 | 7.3 |
| 13 | 5.2 |
| 16 | 7.1 |
| 18 | 6.8 |
| 19 | 6.2 |
| 21 | 5.9 |

The compounds of the examples were also tested in a $CCK_A$ binding assay as follows:

The pancreatata were removed from male guinea-pigs (200–300 g; Dunkin Hartley) and placed in ice-cold HEPES buffer (pH 7.2@21°±3°). The pancreatata were homogenised in 40 ml ice-cold HEPES buffer using a polytron (Brinkmann, PT10, setting 10) 4×1 second. The homogenate was centrifuged at 39,800 g for 15 min at 4°. The supernatant was discarded and the pellet re-suspended using a Teflon-in-glass homogeniser in 20 volumes of fresh buffer and re-centrifuged as above. The final pellet was re-suspended using a Teflon-in-glass homogeniser to a tissue concentration of 1 mg ml$^{-1}$ (original wet weight), and filtered through 500 μm pore-size Nytex mesh.

The membranes (400 μl; containing 0.375 μM PD134, 308) are incubated for 150 minutes at 21°±3° in a final volume of 0.5 ml with HEPES buffer containing [$^{125}$I]—$CCK_8$(S) (50 μl; 200 pM) and competing compound. Total and non-specific binding of [$^{125}$I]—$CCK_8$(S) are defined using 50 μl of buffer and 50 μl of 100 nM L-364,718 respectively. The assay is terminated by rapid filtration through pre-soaked Whatman GF/B filters using a Brandell Cell Harvester. The filters were washed (3×3 ml) with ice-cold 50 mM Tris HCl (pH 7.4 at 4°) and bound radioactivity is determined by counting (1 min) in a gamma counter.

The results are set out in Table 2.

TABLE 2

| Example | $pK_i$ $CCK_A$ |
|---------|----------------|
| 1 | 6.6 |
| 2 | 6.8 |

TABLE 2-continued

| Example | pK$_i$ CCK$_A$ |
|---|---|
| 3 | 6.0 |
| 4 | 6.9 |
| 5 | 6.0 |
| 6 | 6.3 |
| 7 | 5.5 |
| 8 | 5.6 |
| 9 | 6.4 |
| 10 | 7.3 |
| 11 | 6.8 |
| 12 | 6.9 |
| 13 | 5.2 |
| 14 | 5.0 |
| 15 | 5.0 |
| 16 | 7.4 |
| 17 | 5.9 |
| 18 | 6.2 |
| 19 | 5.8 |
| 20 | 5.7 |
| 21 | 5.7 |

Selectivity testing

The compounds were assayed for selectivity with respect to the CCK$_B$ receptor in mouse cortical membranes by means of a radioligand binding assay. The procedure was as follows:

The whole brains from male mice (CDI 22–25 g; Charles River) were removed and placed in ice-cold buffer (pH 7.2 at 21°±3° C.) of the following composition (mM); 10 HEPES, 130 NaCl, 4.7 KCl, 5 MgCl$_2$, 1 EDTA and containing 0.25 g. l$^{-1}$ bacitracin.

The cortex was dissected, weighed and homogenised in 40 ml ice-cold buffer using a Teflon-in-glass homogeniser. The homogenate was centrifuged at 39,800 g for 20 min at 4° C., the supernatant discarded and the pellet resuspended by homogenisation in fresh buffer. The homogenate was recentrifuged (39,800 g; 20 min at 4° C.) and the final pellet was resuspended in HEPES buffer to give a tissue concentration of 2 mg ml$^{-1}$ (original wet weight).

The membranes (400 μl) were incubated for 150 min at 21°±3° C. in a final volume of 0.5 ml with HEPES buffer containing [$^{125}$I] CCK-8S (0.05 ml; 200 pM NEN 2200Ci.mmol$^{-1}$) and competing compound. Total and non-specific binding of [$^{125}$I] CCK-8S were defined using 0.05 ml of buffer and 0.05 ml of 10 mM L-365,260, respectively. The assay was terminated by rapid filtration through pre-soaked Whatman GF/B filters using a Brandell Cell harvester. The filters were washed (3×3 ml) with ice-cold 50 mM Tris-HCl (pH 7.4 at 4° C.) and bound radioactivity determined by counting (1 min.) in a gamma counter.

The results obtained from the CCK$_B$ assay are set out in Table 3.

TABLE 3

| Example | pK$_i$ CCK$_B$ |
|---|---|
| 1 | 5.1 |
| 2 | 5.4 |
| 3 | 4.6 |
| 4 | 5.3 |
| 5 | 4.0 |
| 6 | 4.6 |
| 7 | 4.3 |
| 8 | 4.4 |
| 9 | 5.4 |
| 10 | 5.2 |
| 11 | 4.6 |
| 12 | 5.1 |

TABLE 3-continued

| Example | pK$_i$ CCK$_B$ |
|---|---|
| 13 | 5.0 |
| 15 | 4.6 |
| 16 | 5.0 |
| 17 | 5.7 |
| 18 | 5.5 |
| 19 | 5.5 |
| 20 | 4.7 |
| 21 | 5.0 |

I claim:

1. A compound of the formula

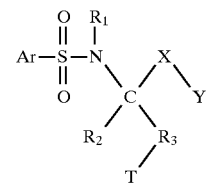

II wherein

Ar is selected from the group consisting of naphthyl, naphthylmethyl, 1,2,3,4-tetrahydronaphthyl, phenethyl, styryl, and indanyl and is optionally substituted by from 1 to 3 substituents selected from the group consisting of C$_1$ to C$_6$ alkyl, C$_1$ to C$_6$ alkoxy, C$_1$ to C$_6$ alkylthio, carboxy, C$_1$ to C$_6$ carboalkoxy, nitro, trihalomethyl, hydroxy, amino, C$_1$ to C$_6$ alkylamino, di(C$_1$ to C$_6$ alkyl)amino, aryl, C$_1$ to C$_6$ alkylaryl, halo, sulfamoyl and cyano;

R$_1$ is H, C$_1$ to C$_6$ alkyl, C$_1$ to C$_6$ alkenyl, cycloalkyl, —(CH$_2$)$_q$ aryl, or —(CH$_2$)$_q$ aryl substituted by 1 to 3 substituents selected from the group consisting of C$_1$ to C$_6$ alkyl, C$_1$ to C$_6$ alkoxy, C$_1$ to C$_6$ alkylthio, carboxy, C$_1$ to C$_6$ carboalkoxy, nitro, trihalomethyl, hydroxy, amino, C$_1$ to C$_6$ alkylamino, di(C$_1$ to C$_6$ alkyl)amino, aryl, C$_1$ to C$_6$ alkylaryl, halo, sulfamoyl and cyano, wherein q is 0 to 4;

R$_2$ is H, methyl or ethyl;

R$_3$ is C$_1$ to C$_3$ alkylene or is absent;

T is carboxyl, —CONR$_4$R$_5$ wherein R$_4$ and R$_5$ are independently H or C$_1$ to C$_4$ alkyl or tetrazolyl;

X is —C(O)— or —CH$_2$—; and

Y is —NR$_6$R$_7$ or —O—R$_6$ wherein R$_6$ and R$_7$ are independently H, C$_1$ to C$_{15}$ hydrocarbyl or halo-substituted C$_1$ to C$_{15}$ hydrocarbyl in which up to 6 carbon atoms may be replaced by —O—, —S—, or —NR$_8$— (R$_8$ being absent or selected from H, C$_1$ to C$_{12}$ hydrocarbyl, C$_1$ to C$_{12}$ hydrocarbyloxycarbonyl and C$_1$ to C$_{12}$ hydrocarbyloxycarbonyl, provided that neither R$_6$ and R$_7$ contains a —O—O— group, and wherein R$_6$ and R$_7$ may be linked by a single or double bond, or a pharmaceutically acceptable salt thereof, provided that when X is —C(O)— and R$_3$ is —(CH$_2$)$_n$— wherein n is from 0 to 3, Y is not

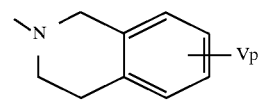

-continued
or

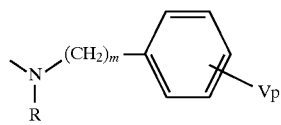

wherein

R is H, $C_1$ to $C_5$ alkyl, —$(CH_2)_r$-aryl or —$(CH_2)_r$-aryl substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, r being from 0 to 4;

V is $C_1$ to $C_4$ alkyl, $C_1$ to $C_4$ alkoxy, $C_1$ to $C_4$ alkylthio, carboxy, $C_1$ to $C_4$ carboalkoxy, nitro, trihalomethyl, hydroxy, —$NR_9R_{10}$, $R_9$ and $R_{10}$ being independently H or $C_1$ to $C_4$ alkyl, $C_1$ to $C_4$ alkylaryl in which aryl is substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, $C_1$ to $C_4$ alkylaryl, or halo;

m is 1 to 3; and p is 0 to 3.

2. A compound according to claim 1 wherein $R_6$ is a saturated group.

3. A compound according to claim 1 wherein $R_7$ is a saturated group.

4. A compound according to claim 1 wherein $R_6$ and $R_7$ are linked to form a saturated carbocyclic or heterocyclic group.

5. A compound according to claim 1 wherein $R_6$ and $R_7$ are not linked.

6. A compound according to claim 1 wherein $R_6$ contains from 1 to 3 heteroatoms.

7. A compound according to claim 6 wherein the heteroatoms are oxygen atoms.

8. A compound according to claim 1 wherein $R_6$ contains no heteroatoms.

9. A compound according to claim 1 wherein $R_7$ contains from 1 to 3 heteroatoms.

10. A compound according to claim 9 wherein the heteroatoms are oxygen atoms.

11. A compound according to claim 1 wherein $R_7$ contains no heteroatoms.

12. A compound according to claim 1 wherein $R_6$ and $R_7$ are linked to form a cyclic group containing from 1 to 3 heteroatoms in addition to the nitrogen atom to which $R_6$ and $R_7$ are linked.

13. A compound according to claim 12 wherein said heteroatoms are oxygen atoms.

14. A compound according to claim 1 wherein $R_6$ and $R_7$ are linked to form a cyclic group containing no heteroatoms, other than the nitrogen atom to which $R_6$ and $R_7$ are linked.

15. A compound according to claim 1 wherein X is —C(O)—.

16. A method of making a compound according to claim 1, which method comprises the step of reacting a suitably protected compound of the formula

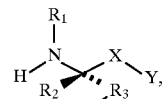

with a compound of the formula $ArSO_2Cl$ in the presence of a base, wherein Ar, $R_1$, $R_2$, $R_3$, X and Y are as defined in claim 1, and Z is a protected carboxyl group, —$CONR_4R_5$ (wherein $R_4$ and $R_5$ are as defined in claim 1 or a tetrazolyl group.

17. A method of making a compound according to claim 1 wherein X is —C(O)—, which method comprises the step of reacting a compound of the formula

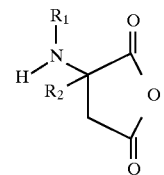

with a compound of the formula HY, wherein Ar, $R_1$, $R_2$, and Y are as defined in claim 1.

18. A method of making a compound according to claim 1, which method comprises the step of reacting a compound of the formula

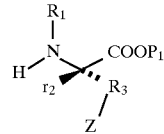

with a compound of the formula $ArSO_2Cl$ in the presence of a base, wherein

Ar is selected from the group consisting of naphthyl, naphthylmethyl, 1,2,3,4-tetrahydronaphthyl, phenethyl, styryl, and indanyl and is optionally substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

$R_1$ is H, $C_1$ to $C_6$ alkyl, $C_1$ to $C_6$ alkenyl, cycloalkyl, —$(CH_2)_q$ aryl, or —$(CH_2)_q$ aryl substituted by 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, wherein q is 0 to 4;

$R_2$ is H, methyl or ethyl;

$R_3$ is $C_1$ to $C_3$ alkylene or is absent;

Z is a protected carboxyl group, —$CONR_4R_5$, where $R_4$ and $R_5$ are independently H or $C_1$ to $C_4$ alkyl or a tetrazolyl group; and $P_1$ is a protecting group.

19. A pharmaceutical composition, comprising a cholecystokinin inhibiting amount of a compound according to claim 1, and a pharmaceutically acceptable carrier or diluent.

20. A compound according to claim 1, wherein Y is —$NR_6R_7$ or, when T is tetrazolyl, Y is —O—$R_6$, wherein $R_6$ and $R_7$ are independently H, $C_1$ to $C_{15}$ hydrocarbyl or halo-substituted $C_1$ to $C_{15}$ hydrocarbyl and wherein $R_6$ and $R_7$ may be linked by a single or double bond.

21. A compound according to claim 20, wherein $C_1$ to $C_{15}$ hydrocarbyl is alkyl, alkenyl, alkynyl, cycloalkyl, cycloalkyl, cycloalkenyl, aryl, alkylaryl, alkenylaryl, alkynylaryl, cycloalkylaryl and cycloalkenylaryl.

22. A compound of the formula

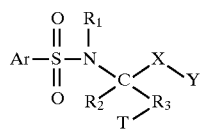     II wherein

Ar is selected from the group consisting of naphthyl, naphthylmethyl, 1,2,3,4-tetrahydronaphthyl, phenethyl, styryl, and indanyl and is optionally substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

$R_1$ is H, $C_1$ to $C_6$ alkyl, $C_1$ to $C_6$ alkenyl, cycloalkyl, —$(CH_2)_q$ aryl, or —$(CH_2)_q$ aryl substituted by 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, wherein q is 0 to 4;

$R_2$ is H, methyl or ethyl;

$R_3$ is $C_1$ to $C_3$ alkylene or is absent;

T is carboxyl, —$CONR_4R_5$ wherein $R_4$ and $R_5$ are independently H or $C_1$ to $C_4$ alkyl, tetrazolyl or —$COOR_{13}$ wherein $R_{13}$ is $C_1$ to $C_4$ alkyl, benzyl or benzyl substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

X is —C(O)— or —$CH_2$—; and

Y is —$NR_6R_7$ or —O—$R_6$ wherein $R_6$ and $R_7$ are independently H, $C_1$ to $C_{15}$ hydrocarbyl or halo-substituted $C_1$ to $C_{15}$ hydrocarbyl in which up to 6 carbon atoms may be replaced by —O—, —S—, or —$NR_8$— ($R_8$ being absent or selected from H, $C_1$ to $C_{12}$ hydrocarbyl, $C_1$ to $C_{12}$ hydrocarbyloxycarbonyl and $C_1$ to $C_{12}$ hydrocarbyloxycarbonyl, provided that neither $R_6$ and $R_7$ contains a —O—O— group, and wherein $R_6$ and R7 may be linked by a single or double bond, or a pharmaceutically acceptable salt thereof, provided that Ar is not 1-naphthyl, 1-naphthylmethyl or 1-(1,2,3,4-tetrahydronaphthyl), and that when (a) $R_3$ is —$(CH_2)_n$— wherein n is from 0 to 3; (b) X is —C(O)—; (c) $R_1$ is not —$(CH_2)_q$(substituted heterocyclic); (d) T is $COOR_{13}$ and [(d)] (e) Y is

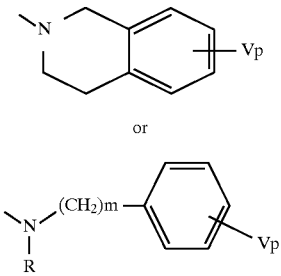

wherein

R is H, $C_1$ to $C_5$ alkyl, —$(CH_2)_r$-aryl or —$(CH_2)_r$-aryl substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, r being from 0 to 4;

V is $C_1$ to $C_4$ alkyl, $C_1$ to $C_4$ alkoxy, $C_1$ to $C_4$ alkylthio, carboxy, $C_1$ to $C_4$ carboalkoxy, nitro, trihalomethyl, hydroxy, —$NR_9R_{10}$, $R_9$ and $R_{10}$ being independently H or $C_1$ to $C_4$ alkyl, $C_1$ to $C_4$ alkylaryl in which aryl is substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, $C_1$ to $C_4$ alkylaryl, or halo;

m is 1 to 3; and p is 0 to 3, then $R_{13}$ is selected from $C_1$ to $C_4$ alkyl and substituted benzyl, and further provided that T is not carboxyl when X is —C(O)— and Y is —OH.

23. A method of treating the physiological effects of cholecystokinin or gastrin in a patient, comprising the step of administering to a patient, suffering from a condition which can be alleviated by counteracting the effects of cholecystokinin or gastrin, an effective cholecystokinin inhibiting amount of a compound of the formula

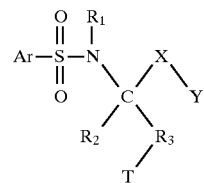     II wherein

Ar is selected from the group consisting of naphthyl, naphthylmethyl, 1,2,3,4-tetrahydronaphthyl, phenethyl, styryl, and indanyl and is optionally substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

$R_1$ is H, $C_1$ to $C_6$ alkyl, $C_1$ to $C_6$ alkenyl, cycloalkyl, —$(CH_2)_q$ aryl, or —$(CH_2)_q$ aryl substituted by 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, wherein q is 0 to 4;

$R_2$ is H, methyl or ethyl;

$R_3$ is $C_1$ to $C_3$ alkylene or is absent;

T is carboxyl, —$CONR_4R_5$ wherein $R_4$ and $R_5$ are independently H or $C_1$ to $C_4$ alkyl, tetrazolyl or —$COOR_{13}$ wherein $R_{13}$ is $C_1$ to $C_4$ alkyl, benzyl or benzyl substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

X is —C(O)— or —$CH_2$—; and

Y is —$NR_6R_7$ or —O—$R_6$ wherein $R_6$ and $R_7$ are independently H, $C_1$ to $C_{15}$ hydrocarbyl or halo-substituted $C_1$ to $C_{15}$ hydrocarbyl in which up to 6 carbon atoms may be replaced by —O—, —S—, or —$NR_8$— ($R_8$ being absent or selected from H, $C_1$ to $C_{12}$ hydrocarbyl, $C_1$ to $C_{12}$ hydrocarbyloxycarbonyl and $C_1$ to $C_{12}$ hydrocarbyloxycarbonyl, provided that neither $R_6$ and $R_7$ contains a —O—O— group, and wherein $R_6$ and $R_7$ may be linked by a single or double bond, or a pharmaceutically acceptable salt thereof, provided that Ar is not 1-naphthyl, 1-naphthylmethyl or 1-(1,2,3,4-tetrahydronaphthyl), and that when (a) $R_3$ is —$(CH_2)_n$— wherein n is from 0 to 3; (b) X is —C(O)—; (c) $R_1$ is not —$(CH_2)_q$(substituted heterocyclic); (d) T is —$COOR_{13}$; and (e) Y is

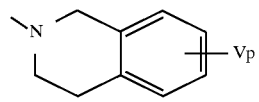

or

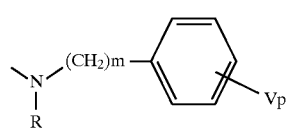

wherein

R is H, $C_1$ to $C_5$ alkyl, —$(CH_2)_r$-aryl or —$(CH_2)_r$-aryl substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, r being from 0 to 4;

V is $C_1$ to $C_4$ alkyl, $C_1$ to $C_4$ alkoxy, $C_1$ to $C_4$ alkylthio, carboxy, $C_1$ to $C_4$ carboalkoxy, nitro, trihalomethyl, hydroxy, —$NR_9R_{10}$, $R_9$ and $R_{10}$ being independently H or $C_1$ to $C_4$ alkyl, $C_1$ to $C_4$ alkylaryl in which aryl is substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, $C_1$ to $C_4$ alkylaryl, or halo;

m is 1 to 3; and p is 0 to 3, then $R_{13}$ is selected from $C_1$ to $C_4$ alkyl and substituted benzyl, and that T is not carboxyl when X is —C(O)— and Y is —OH.

24. A method of treating the physiological effects of cholecystokinin or gastrin in a patient, comprising the step of administering to a patient, suffering from a condition which can be alleviated by counteracting the effects of cholecystokinin or gastrin, an effective cholecystokinin inhibiting amount of a compound of the formula

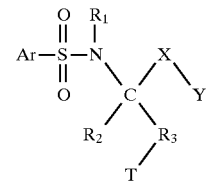

II wherein

Ar is selected from the group consisting of naphthyl, naphthylmethyl, 1,2,3,4-tetrahydronaphthyl, phenethyl, styryl, and indanyl and is optionally substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

$R_1$ is H, $C_1$ to $C_6$ alkyl, $C_1$ to $C_6$ alkenyl, cycloalkyl, —$(CH_2)_q$ aryl, or —$(CH_2)_q$ aryl substituted by 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, wherein q is 0 to 4;

$R_2$ is H, methyl or ethyl;

$R_3$ is $C_1$ to $C_3$ alkylene or is absent;

T is carboxyl, —$CONR_4R_5$ wherein $R_4$ and $R_5$ are independently H or $C_1$ to $C_4$ alkyl or tetrazolyl;

X is —C(O)— or —$CH_2$—; and

Y is —$NR_6R_7$ or —O—$R_6$ wherein $R_6$ and $R_7$ are independently H, $C_1$ to $C_{15}$ hydrocarbyl or halo-substituted $C_1$ to $C_{15}$ hydrocarbyl in which up to 6 carbon atoms may be replaced by —O—, —S—, or —$NR_8$— ($R_8$ being absent or selected from H, $C_1$ to $C_{12}$ hydrocarbyl, $C_1$ to $C_{12}$ hydrocarbyloxycarbonyl and $C_1$ to $C_{12}$ hydrocarbyloxycarbonyl, provided that neither $R_6$ and $R_7$ contains a —O—O— group, and wherein $R_6$ and $R_7$ may be linked by a single or double bond, or a pharmaceutically acceptable salt thereof, provided that when X is —C(O)— and $R_3$ is —$(CH_2)_n$- wherein n is from 0 to 3, Y is not

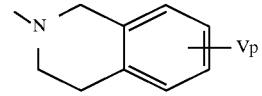

or

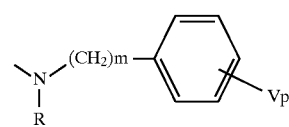

wherein

R is H, $C_1$ to $C_5$ alkyl, —$(CH_2)_r$-aryl or —$(CH_2)_r$-aryl substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, r being from 0 to 4;

V is $C_1$ to $C_4$ alkyl, $C_1$ to $C_4$ alkoxy, $C_1$ to $C_4$ alkylthio, carboxy, $C_1$ to $C_4$ carboalkoxy, nitro, trihalomethyl, hydroxy, —$NR_9R_{10}$, $R_9$ and $R_{10}$ being independently H or $C_1$ to $C_4$ alkyl, $C_1$ to $C_4$ alkylaryl in which aryl is substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, $C_1$ to $C_4$ alkylaryl, or halo;

m is 1 to 3; and p is 0 to 3.

25. A method of treating the physiological effects of cholecystokinin or gastrin in a patient, comprising the step of administering to a patient, suffering from a condition which can be alleviated by counteracting the effects of cholecystokinin or gastrin, an effective cholecystokinin inhibiting amount of a compound of the formula

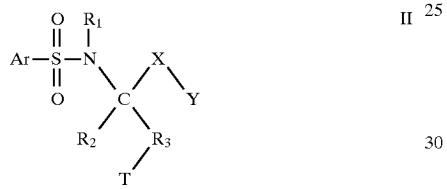

II wherein

Ar is selected from the group consisting of naphthyl, naphthylmethyl, 1,2,3,4-tetrahydronaphthyl, phenethyl, styryl, and indanyl and is optionally substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

$R_1$ is H, $C_1$ to $C_6$ alkyl, $C_1$ to $C_6$ alkenyl, cycloalkyl, —$(CH_2)_q$ aryl, or —$(CH_2)_q$ aryl substituted by 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, wherein q is 0 to 4;

$R_2$ is H, methyl or ethyl;

$R_3$ is $C_1$ to $C_3$ alkylene or is absent;

T is carboxyl, —$CONR_4R_5$ wherein $R_4$ and $R_5$ are independently H or $C_1$ to $C_4$ alkyl, tetrazolyl, or —$COOR_{13}$ wherein $R_{13}$ is $C_1$ to $C_4$ alkyl, benzyl or benzyl substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

X is —C(O)— or —$CH_2$—; and

Y is —$NR_6R_7$ or —O—$R_6$ wherein $R_6$ and $R_7$ are independently H, $C_1$ to $C_{15}$ hydrocarbyl or halo-substituted $C_1$ to $C_{15}$ hydrocarbyl in which up to 6 carbon atoms may be replaced by —O—, —S—, or —$NR_8$— ($R_8$ being absent or selected from H, $C_1$ to $C_{12}$ hydrocarbyl, $C_1$ to $C_{12}$ hydrocarbyloxycarbonyl and $C_1$ to $C_{12}$ hydrocarbyloxycarbonyl, provided that neither $R_6$ and $R_7$ contains a —O—O— group, and wherein $R_6$ and $R_7$ may be linked by a single or double bond, or a pharmaceutically acceptable salt thereof, provided that when X is —C(O)— and $R_3$ is —$(CH_2)_n$- wherein n is from 0 to 3, Y is not

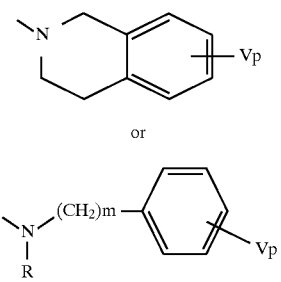

wherein

R is H, $C_1$ to $C_5$ alkyl, —$(CH_2)_r$-aryl or —$(CH_2)_r$-aryl substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, r being from 0 to 4;

V is $C_1$ to $C_4$ alkyl, $C_1$ to $C_4$ alkoxy, $C_1$ to $C_4$ alkylthio, carboxy, $C_1$ to $C_4$ carboalkoxy, nitro, trihalomethyl, hydroxy, —$NR_9R_{10}$, $R_9$ and $R_{10}$ being independently H or $C_1$ to $C_4$ alkyl, $C_1$ to $C_4$ alkylaryl in which aryl is substituted by from 1 to 3 substituents selected from the group consisting of $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano, $C_1$ to $C_4$ alkylaryl, or halo;

m is 1 to 3; and p is 0 to 3.

* * * * *